(12) United States Patent
Menn

(10) Patent No.: US 8,562,512 B2
(45) Date of Patent: Oct. 22, 2013

(54) ENDOSCOPIC TOOL ASSEMBLY

(75) Inventor: Pavel Menn, Marblehead, MA (US)

(73) Assignee: Microline Surgical, Inc., Beverly, MA (US)

( * ) Notice: Subject to any disclaimer, the term of this patent is extended or adjusted under 35 U.S.C. 154(b) by 2031 days.

(21) Appl. No.: 11/746,284

(22) Filed: May 9, 2007

(65) Prior Publication Data
US 2008/0281299 A1    Nov. 13, 2008

(51) Int. Cl.
*A61B 1/00* (2006.01)

(52) U.S. Cl.
USPC .............................. 600/104; 600/102; 600/153

(58) Field of Classification Search
USPC ............ 600/104, 105, 114, 125, 156; 24/339, 24/347, 374; 206/364
See application file for complete search history.

(56) References Cited

U.S. PATENT DOCUMENTS

| | | | | |
|---|---|---|---|---|
| 1,816,301 | A | * | 7/1931 | Sundell ............................ 24/339 |
| D291,728 | S | | 9/1987 | Hoyt |
| 5,115,542 | A | * | 5/1992 | Gehres ............................ 24/543 |
| 5,685,822 | A | * | 11/1997 | Harhen .......................... 600/125 |
| 6,071,233 | A | * | 6/2000 | Ishikawa et al. .............. 600/104 |
| 6,277,131 | B1 | | 8/2001 | Kalikow |
| 6,569,085 | B2 | * | 5/2003 | Kortenbach et al. .......... 600/104 |
| 6,620,184 | B2 | | 9/2003 | De Laforcade et al. |
| 2005/0234297 | A1 | | 10/2005 | Devierre et al. |

OTHER PUBLICATIONS

U.S. Appl. No. 11/746,257, filed May 9, 2007, Menn.

* cited by examiner

*Primary Examiner* — Alireza Nia
(74) *Attorney, Agent, or Firm* — Greenblum & Bernstein P.L.C.

(57) ABSTRACT

A surgical tool assembly is provided having a surgical tool, a scope; and a detachable clip which couples the tool and scope. The clip includes a first grip which engages a peripheral surface of the tool and a second grip which engages a peripheral surface of the scope. Additionally, the first and second grips may be formed continuously with one another.

19 Claims, 3 Drawing Sheets

ENDOSCOPIC TOOL ASSEMBLY

BACKGROUND OF THE INVENTION

1. Field of the Invention

The present invention relates to an endoscopic tool assembly, and more particularly, to a clip which detachably couples a endoscopic tool and an endoscope to provide an endoscopic tool assembly.

2. Description of the Background Art

Endoscopic surgery has recently become a widely-practiced surgical procedure. For example, laparoscopic surgery (i.e., one type of endoscopic surgery) generally involves small incisions through the navel and abdominal wall to view or operate on organs or tissue located in the abdominal cavity. Additionally, a camera, optical fiber or lens (i.e., scope) is placed in the area to aid the surgeon in guiding the endoscopic instrument to the particular area to be observed or operated upon.

In the conventional art, endoscopic surgery is generally preformed using elongated instruments slidably inserted through a trocar. The trocar generally includes a cannula or trocar sleeve (i.e., a hollow sheath or sleeve with a central lumen) and a sharp obturator received in the cannula. The trocar may be used to penetrate the abdominal wall or chest. The obturator is withdrawn from the cannula after the intra-abdominal end of the trocar is in the abdominal cavity, and the cannula remains in the abdominal wall throughout the surgical procedure, allowing the introduction of various surgical instruments (e.g., an endoscopic tool). Trocars are available in different sizes, as are cannulae, to accommodate various instruments. However, in some cases endoscopic surgery is performed in a naturally-occurring body cavity (e.g., the uterus).

Manipulation of the instruments (including an endoscopic tool) during endoscopic surgery is generally observed through the scope which may be inserted through a separate trocar into the operating cavity. Alternatively, the scope may be contained within a surgical tube which also contains surgical instruments. In any event, the operator must perform the surgical manipulations using an effector unit, such as scissors, dissectors, graspers and retractors located on the end of the surgical instrument remotely located from the operator's hands and confined within a relatively small cavity created for the operation. Therefore, the images provided by the endoscope must be accurate and reliable.

However, because the endoscope is typically inserted into the surgical area adjacent to the surgical instrument, the parallax resulting from the acute angle formed between the endoscope and the surgical instrument may restrict or distort the surgeon's view of the surgical site. Thus, the surgeon may have only a limited view of the working end of the surgical instrument.

Further, because the endoscopic tool must often be rotated to perform an appropriate surgical procedure, what is needed in the art is a surgical instrument assembly or clip, which is capable of reliably and accurately detachably coupling a scope and an endoscopic tool such that relative movement between the endoscope and endoscopic tool, as well as undesirable parallax resulting from an acute angle formed between the endoscope and endoscopic tool, may be prevented.

SUMMARY OF THE INVENTION

Accordingly, a non-limiting feature of the present invention provides a surgical instrument assembly including a clip, an endoscopic tool, and an endoscope coupled together, thereby allowing for accurate positioning and reliable coupling between the instruments. Thus, the negative effects caused by parallax may be prevented.

Another feature of the present invention provides a clip which accurately and reliably couples an endoscope and an endoscopic tool. Thus, existing endoscopic tools, whether single or multiple use, may be retrofitted with an endoscope.

A non-limiting feature of the present invention provides an endoscopic tool assembly including a clip for coupling an endoscopic tool and an endoscope together. As described herein, the term "endoscope" includes all types of scopes to be used in surgical procedures, including but not limited to cameras, endoscopes, and fiber scopes. The endoscopic tool assembly includes a surgical tool, a scope; and a detachable clip which couples the tool and the scope, the clip may have a first opening (i.e., grip) which engages a surface (e.g. an outer surface) of the tool and a second opening (i.e., grip) which engages a surface (e.g., an outer surface) of the scope. Additionally, the first and second openings maybe formed continuously with one another, and the clip may include a bottom opening.

According to an additional feature, the first opening may be provided with a knurled surface which engages said peripheral surface of said tool. Additionally, the knurled surface may include generally elongated protrusions extending in a direction generally perpendicular to a first diameter of the first opening. Further, the elongated protrusions may have a generally triangular cross-section.

In an additional feature, the knurled surface may be provided only on a portion of a circumference of the first opening. Further, the clip may include generally oppositely facing first and second lobes provided on a circumference of the first opening. Additionally, the clip may have generally oppositely facing third and fourth lobes provided on a circumference of the second opening. In accordance with another feature, the first and second lobes may be formed larger than each of the third and fourth lobes.

According to an additional feature, the clip may be formed of a resilient material.

In yet still another feature, the first lobe, the second lobe, and the first opening together may form a upper clip body. Further, similar to the upper clips body, the third lobe, the fourth lobe, and the second opening together may form a lower clip body. Additionally, a concavity may connect the upper clip body to the lower clip body thereby forming a generally mushroom-shape. Further, the assembly may include a sheath configured to be inserted into a mammalian body, and an inner surface of the sheath may be configured to engage an outer surface of the clip.

Another feature includes, the upper body being formed having a generally semi-circular shape. In an additional feature, the second opening may be provided between the concavity and the bottom opening; wherein the first and second openings are provided next to each other such that the first radial center of the first opening is radially spaced from the second radial center of the second opening. Additionally, the first diameter may be larger than the second diameter.

In an additional feature, the first opening may be provided in an upper clip body and the second opening may be provided in a lower clip body. In this regard, the concavity hingedly connects the upper clip body to the lower clip body. Further, the second opening may be configured to contract and expand due to the flexing of the concavity. Additionally, the upper clip body may include a connector which hingedly connects a first half of the clip to a second half of the clip. In this regard, the first and second halves may be generally mirror images of each other. Additionally, the first opening may be configured to contract and expand due to the flexing of the connector.

In a further embodiment, an endoscopic tool assembly may include a surgical tool, a scope, and a detachable clip which couples the tool and scope. Further, the clip may have a generally cylindrical body including first and second openings (i.e., grips) which engage the surgical tool and scope, respectively. Additionally, a surface (e.g., an outer surface) of the cylindrical body may be configured to engage an inner surface (e.g., a circumferential inner surface) of a sheath which is configured to receive the tool assembly therein.

Another feature includes providing the first opening with a knurled surface which engages a peripheral surface of the tool. Additionally, the knurled surface may have generally elongated protrusions extending in a direction generally perpendicular to a first diameter of the first grip, and the elongated protrusions may have a generally triangular cross-section. Further, the knurled surface may be provided only on a portion of a circumference of the first opening. Additionally, as in the case of the first embodiment, the clip may be formed of a resilient material.

According to an additional feature, the first and second opening may be formed continuously with one another, and the clip may include spaced apart distal ends. Further, the first opening may have a first radial center and a first diameter, and the second opening may have a second radial center and a second diameter. In this regard, the second may be provided between the concavity and the distal ends. Further, the first and second openings may be provided next to each other such that the first radial center of the first opening is radially spaced from said second radial center of the second opening, and the first diameter may be larger than the second diameter.

Additionally, the tool may be actuable within a patient's body, and may be one of a clip applier, forceps, scissors, grasper, punch (e.g., biopsy punch), specula (e.g., endocervical specula), a laparoscopic instrument, or clamp (e.g., a hysterectomy clamp).

Other exemplary embodiments and advantages of the present invention may be ascertained by reviewing the present disclosure and the accompanying drawings, and the above description should not be considered to limit the scope of the present invention.

BRIEF DESCRIPTION OF THE DRAWINGS

The present invention is further described in the detail description which follows, in reference to the noted plurality of drawings, by way of non-limiting examples of preferred embodiments of the present invention, in which like characters represent like elements throughout the several views of the drawings, and wherein.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
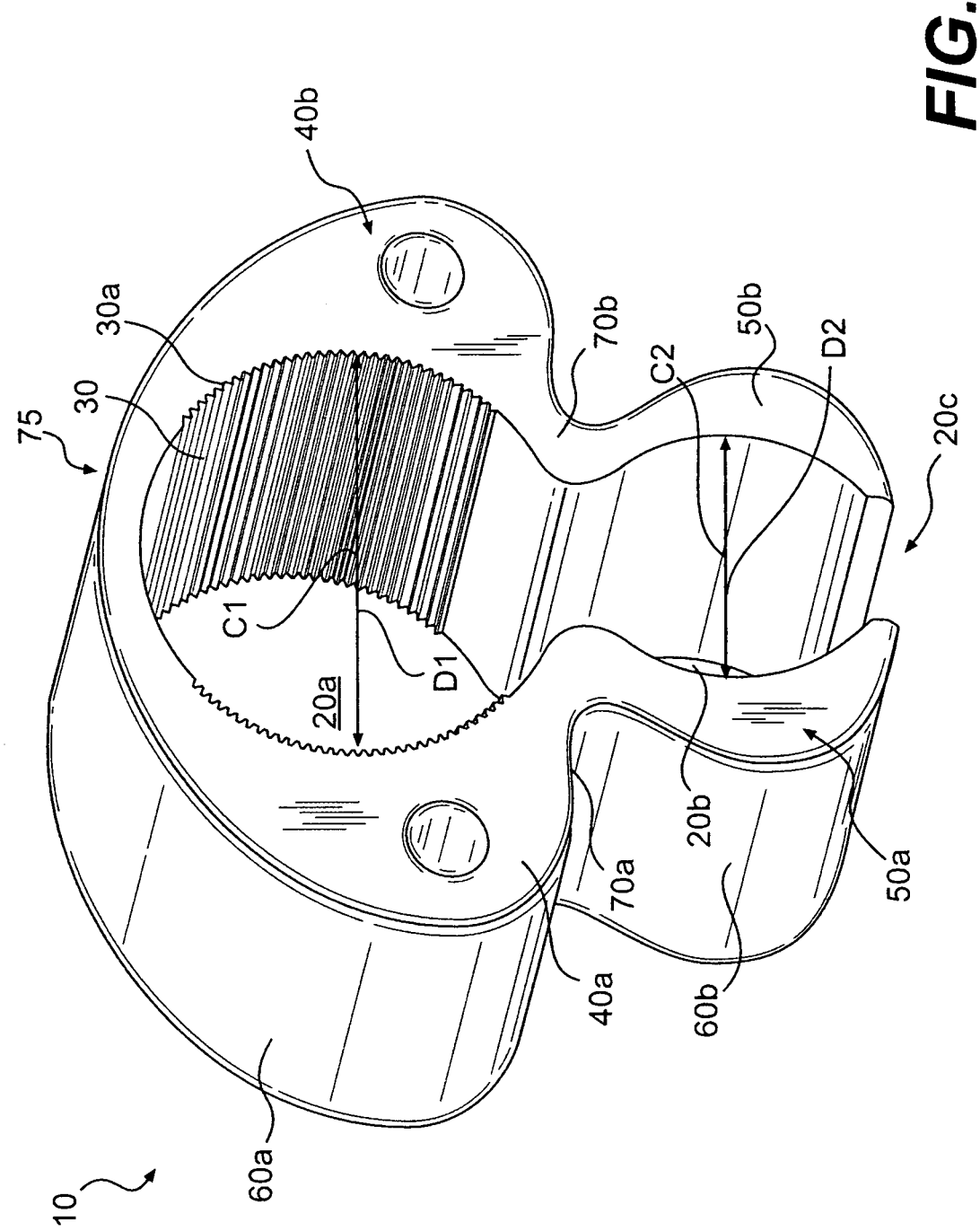
FIG. 1 is a perspective view of a clip of the endoscopic tool assembly according to an embodiment of the present invention.
Figure 2:
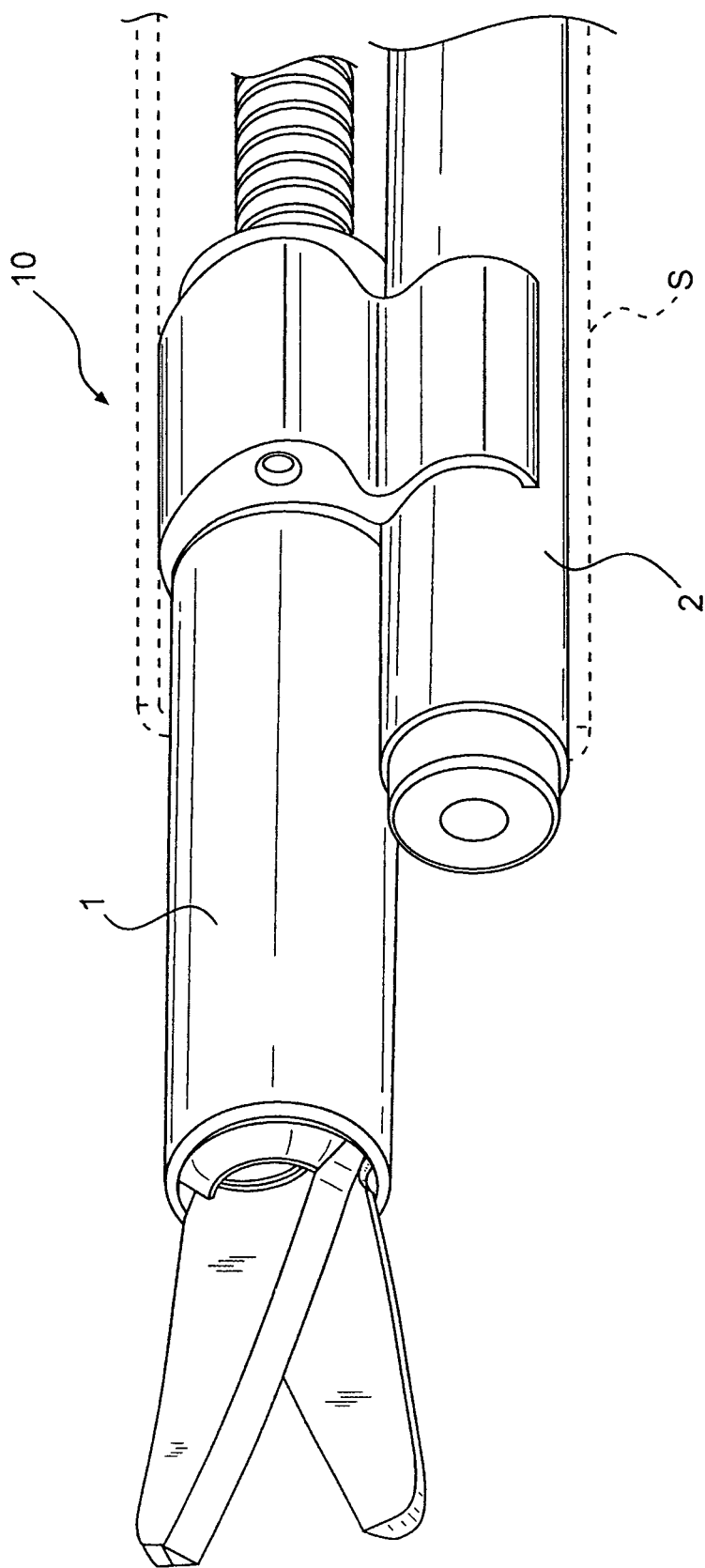
FIG. 2 is a perspective view of the endoscopic tool assembly of the present invention.

Referring to the drawings, wherein like characters represent like elements, FIG. 1 shows a perspective view of a clip 10 of a first embodiment of the endoscopic tool assembly, having first 20a and second 20b openings (i.e., first and second grips) according to a non-limiting embodiment of the present invention. The first opening 20a may have a first radial center $C_1$ and a first diameter $D_1$, and engages a peripheral surface of the endoscopic tool 1. The second opening 20b may have a second radial center $C_2$ and a second diameter $D_2$, and engages a peripheral surface of the endoscope 2 (as illustrated in FIG. 2). The clip 10, when coupling the tool 1 and/or scope 2, is configured to be held within and engage inner surfaces of a sheath S. Further, it is appreciated by one of skill in the art that the sheath S may be configured to be inserted into a mammalian body, and an inner surface of the sheath S may be configured to engage an outer surface of the clip. While FIG. 2 shows the clip being used with a rigid tool 1 and scope 2, those skilled in the art will readily appreciate that flexible tools and scopes may be used with the clip in alternative embodiments. The second opening 20b may be provided between the first opening 20a and a bottom opening 20c of the clip 10. In this regard, the first 20a and second 20b openings may be provided next to each other such that the first radial center $C_1$ of the first opening is radially spaced from the second radial center $C_2$ of the second opening. In addition, the first diameter $D_1$ may be larger than the second diameter $D_2$.

In addition, the first opening 20a may be provided having a knurled surface 30 configured to engage the peripheral (or outer) surface of the endoscopic tool 1 to restrict rotation of the tool within the clip. In this regard, the knurled surface 30 may include generally elongated protrusions 30a extending in a direction generally perpendicular to the first diameter $D_1$ although it is understood by those of skill in the art that the knurled surface may include any surface configured to restrict rotation of the tool 1, including but not limited to circular protrusions, diagonally extending protrusions, and the like. Further, the elongated protrusions 30a may have a generally triangular cross-section although those of skill in the art would appreciate that other suitable cross-sections may be used in alternative embodiments, including but not limited to trapezoidal, semicircular, rectangular and the like. The knurled surface 30 may also be provided only on a portion of a circumference of the first opening 20a. That is, by providing the knurled surface 30 improved engagement between the first opening 20a and an endoscopic tool 1 can be achieve, thereby further preventing, e.g., rotational and translational movement between the clip 10, the endoscopic tool 1, and the endoscope 2. However, one of ordinary skill in the art would recognize that any suitable arrangement or structure for positively coupling the clip to either one of an endoscopic tool or endoscope may be employed without departing from the spirit and scope of the present invention.

Also, in one non-limiting example, the endoscope may be provided having an outer diameter of about 1.0 mm to about 2.0 mm; the tool may be provided having an outer diameter of about 5.0 mm; and the sheath S may be provided having an outer diameter of about 10.0 mm and a length of about eight inches. However, one of ordinary skill in the art would recognize that any suitable size scope, tool, and sheath S may be employed without departing from the spirit and scope of the present invention.

Further, as illustrated in FIG. 1, the clip 10 of the endoscopic tool assembly may be provided with generally oppositely facing first 40a and second 40b lobes provided on a circumference of the first opening 20a. Additionally, generally oppositely facing third 50a and fourth lobes 50b may be provided on a circumference of the second opening 20b. In this regard, each of the first 40a and second lobes 40b may be provided to be larger than each of the third 50a and fourth lobes 50b. The clip 10 may be formed of a resilient material, e.g., plastic, rubber, elastomer, or any other suitable resilient materials and mixtures thereof.

The first lobe 40a, the second lobe 40b, and the first opening 20a together may form a upper clip body 60a; and the third lobe 50a, the fourth lobe 50b, and the second opening 20b together may form a lower clip body 60b. A concavity in the form of concavities 70a, 70b may be provided on each respective side of the clip to connect the upper clip body 60a to the lower clip body 60b thereby forming a generally mushroom-shaped clip 10 which couples the endoscopic tool 1 and the endoscope 2 together. In other words, concavity 70a flexibly connects (e.g., by a living hinge) the first lobe 40a to the third lobe 50a, and concavity 70b flexibly connects (e.g., by a living hinge) the second lobe 40b to the forth lobe 50b. It is appreciated by those skilled in the art that by providing a clip having the aforementioned features, a clip having sufficient strength and resiliency properties can be achieved; thereby ensuring that the clip 10, endoscopic tool 1, and endoscope 2 are reliably coupled together (i.e., thereby forming a secure and reliable endoscopic tool assembly), as illustrated in FIG. 2. It is also appreciated by those skilled in the art that, while a pair of concavities 70a, 70b is shown, a number of cavities which are fewer or greater than the two cavities may be present without departing from the spirit and scope of the present invention.

It is appreciated, by those skilled in the art that the tool may be configured to be any suitable surgical tool. For example, the tool may be a clip applier having a body assembly which may include a handle and a squeezable trigger, a barrel having a first end extending into the body assembly, a pair of jaws arranged on a second end of the barrel, the jaws being actuable by squeezing action of the trigger, the second end of the barrel and the pair of jaws configured to be inserted into a body cavity, and a loading port in communication with the barrel. The barrel may be configured to alternatively accept the insertion, through the loading port, of a first cartridge type containing a plurality of clips of a first size and/or shape, or a second cartridge type containing a plurality of clips of a second size and/or shape, the first size and/or shape being different from the second size and/or shape. Also, the pair of jaws may be configured to accept one clip of the plurality of clips of the first size by opening to a first jaw gap, wherein the pair of jaws is further configured to accept a clip of the plurality of clips of the second size by opening to a second jaw gap. A non-limiting example of such a clip applier is described in U.S. Pat. No. 6,277,131, which is expressly incorporated by reference herein. Additionally, the tool may be configured as a rigid or flexible grasper, as disclosed in U.S. Pat. No. 6,620,184, which is expressly incorporated by reference herein.

Additionally, the upper clip body 60a may be formed having a generally semi-circular shape. In this regard, the first lobe 40a, the second lobe 40b, and the first opening 20a may together form the generally semi-circular shape, thereby providing the clip 10 with appropriate strength characteristics, e.g., for positively retaining the endoscopic tool 1 and coupling the endoscope 2 thereto. However, one of ordinary skill in the art would recognize that any shape of form for positively retaining the endoscopic tool and coupling the endoscope thereto may be employed without departing from the objects of the present invention. Further, it is appreciated by one of skill in the art that the sheath S may be configured to be inserted into a mammalian body, and an inner surface of the sheath S may be configured to engage an outer surface of the clip.

Additionally, as illustrated in FIG. 1 the first opening 20a of the clip 10 may be provided in an upper clip body 60a and the second opening 20b may be provided in a lower clip body 60b. In this regard, the concavities 70a, 70b connect the upper clip body 60a to the lower clip body 60b. Further, the second opening 20b may be configured to contract and expand due to the flexing of the concavities 70a, 70b. Additionally, the upper clip body 60a may include a connector 75 (e.g., a living hinge) which connects a first half of the clip to a second half of the clip. In this regard, the first and second halves may be generally mirror images of each other (i.e., as shown by the symmetrical line "A" in FIG. 1). Additionally, the first opening 20a may be configured to contract and expand due to flexing of the connector 75. In other words, the flexing of the connector 75 causes the distance between the first lobe 40a and second lobe 40b to be adjusted to accommodate a tool. Also, the flexing of the concavities 70a, 70b causes the distance between the third lobe 50a and the fourth lobe 50b to be adjusted to accommodate a scope, without adjusting the distance between the first lobe 40a and the second lobe 40b.

The clip 10 is configured to provide a dual spring function such that the clip can accept tools and scopes of various sizes. Therefore, tools and scopes of various sizes may be used together. That is, the connector 75 may provide the clip with a first spring function by allowing the first opening 20a to contract and expand due to the flexing of the connector 75; and the concavities 70a, 70b may provide the clip with a second spring function by allowing the second opening 20b to contract and expand due to flexing of the concavities 70a, 70b. Because the connector 75 may flex independently of the concavities 70a, 70b, and the concavities 70a, 70b may flex independent of the connector 75, the clip 10 allows for scopes and tools to be used together regardless of the size variations therebetween. For example, a smaller diameter scope may be replaced in the clip with a larger diameter scope, thereby causing the concavities 70a, 70b to flex outwardly to accommodate the larger diameter scope, without causing the connector 75 to flex outwardly as well (which would otherwise loosen the grip of the first opening 20a on the tool 1), allowing both tool and scope to be securely held by the clip. Thus, the tool assembly of the present invention may be provided with a dual spring function.

Figure 3:
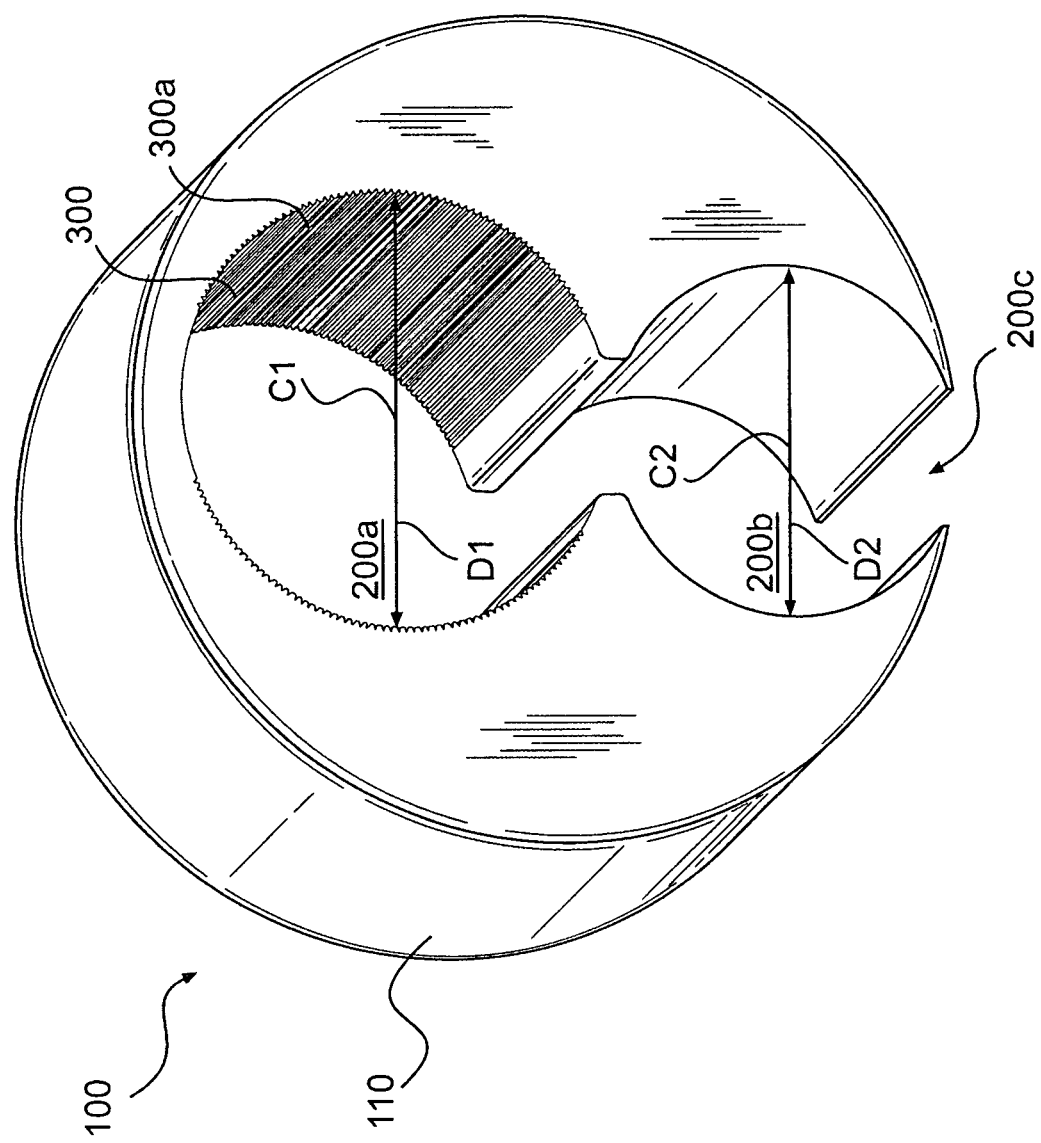
FIG. 3 is a perspective view of a clip of the endoscopic tool assembly according to a second embodiment of the present invention.

As illustrated in the further non-limiting embodiment of FIG. 3, a clip 100 which couples an endoscopic tool 1 and an endoscope 2 together to form an endoscopic tool assembly may be provided having a generally cylindrical body 110. The generally cylindrical body 110 may be provided having first 200a and second 200b openings which engage the endoscopic tool 1 and the endoscope 2, respectively. A peripheral surface of the cylindrical body 110 may be configured to engage an inner circumferential surface of a sheath S configured to receive the endoscopic tool 1 and the endoscope 2 therein, thereby preventing fluid passage between peripheral surfaces of the endoscopic tool 1 and endoscope 2, and an inner circumferential surface of the sheath S. For example, the aforementioned generally cylindrical clip 100 may be provided as a custom clip provided with an outer periphery formed to engage (e.g., to matingly engage) an inner circumferential surface of a sheath employed in a particular application, to thereby prevent the passage of fluid past the clip 100. However, one of ordinary skill in the art would recognize that the cylindrical clip 100 may also be provided in various sizes (i.e., without customization) in which an appropriate size is selected for a suitable application.

Further, as illustrated in FIG. 3, the first opening 200a provided in the generally cylindrical body 110 may also have a knurled surface 300 which engages the peripheral surface of the endoscopic tool 1. The knurled surface 300 may include generally elongated protrusions 300a extending in a direction generally perpendicular to a first diameter $D_1$ of the first opening although the knurled surface may be provided having any suitable shape or form (e.g., circular protrusions, diagonally extending protrusions, and the like). The elongated protrusions 300a may have a generally triangular cross-section, although other suitable cross-sectional configurations may be used, including but not limited to trapezoidal, semicircular, rectangular and the like. Additionally, the knurled surface 300 may be provided only on a portion of a circumference of the first opening 200a. Further, the clip 100 may be formed of a resilient material. However, one of ordinary skill in the art would recognize that any suitable arrangement or structure for positively coupling the clip to either one of an endoscopic tool or endoscope may be employed without departing from the spirit and scope of the present invention.

As illustrated in FIG. 3, the first opening 200a may have a first radial center $C_1$ and a first diameter $D_1$, and the second opening 200b may have a second radial center $C_2$ and a second diameter $D_2$. Further, the second opening 200b may be provided between the first opening 200a and a bottom opening 200c provided in the clip 100. In this regard, the first 200a and second 200b openings may be provided next to each other such that the first radial center $C_1$ of the first opening 200a is radially spaced from the second radial center $C_2$ of the second opening 200b. Additionally, the first diameter $D_1$ may be provided to be larger than the second diameter $D_2$. Further, in an alternative embodiment, the clip 100 may be provided without the bottom opening 200c.

Additionally, the tool may be actuable within a patient's body, and may be any type configured to be used in surgical procedures, including but not limited to a clip applier, forceps, scissors, grasper, punch (e.g., biopsy punch), specula (e.g., endocervical specula), a laparoscopic instrument, or clamp (e.g., a hysterectomy clamp).

Further, one of ordinary skill in the art would appreciate that either one of the clips, 10 and 100, respectively, may be formed with the respective openings (i.e., 20a and 20b, & 200a and 200b) not being in communication with each other (i.e., provided separately with the clip).

It is further noted that the foregoing examples have been provided merely for the purpose of explanation and are in no way to be construed as limiting of the present invention. While the present invention has been described with reference to a preferred embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A surgical tool assembly comprising:
   a surgical tool;
   a scope;
   a detachable clip which couples said tool and scope, said clip having a first grip which engages a surface of said tool and a second grip which engages a surface of said scope, wherein said first and second grips are formed continuously with one another;
   said first grip is provided in an upper clip body and said second grip is provided in a lower clip body, and a concavity hingedly connects said upper clip body to said lower clip body; and
   said upper clip body comprising a connector which hingedly connects a first half of the clip to a second half of the clip, said first and second halves being generally mirror images of each other, wherein
   said connector flexes to provide a spring action allowing said first grip to contract and expand.

2. The surgical tool assembly according to claim 1, wherein said clip comprises a bottom opening.

3. The surgical tool assembly according to claim 1, wherein said first grip comprises a knurled surface which engages said peripheral surface of said tool.

4. The surgical tool assembly according to claim 3, wherein said knurled surface comprises generally elongated protrusions extending in a direction generally perpendicular to a first diameter of said first grip, said elongated protrusions having a generally triangular cross-section.

5. The surgical tool assembly according to claim 3, wherein said knurled surface is provided only on a portion of a circumference of said first grip.

6. The surgical tool assembly according to claim 1, wherein said clip comprises generally oppositely facing first and second lobes provided on a circumference of said first grip.

7. The surgical tool assembly according to claim 1, further comprising a sheath configured to be inserted into a mammalian body, wherein an inner surface of said sheath is configured to engage an outer surface of said clip.

8. The surgical tool assembly according to claim 6, wherein said clip comprises generally oppositely facing third and fourth lobes provided on a circumference of said second grip.

9. The surgical tool assembly according to claim 8, wherein each of said first and second lobes are larger than each of said third and fourth lobes.

10. The surgical tool assembly according to claim 8, wherein said first lobe, said second lobe, and said first grip together form a upper clip body, and wherein said third lobe, said fourth lobe, and said second grip together form a lower clip body.

11. The surgical tool assembly according to claim 1, wherein said upper and lower clip bodies form a generally mushroom-shape.

12. The surgical tool assembly according to claim 10, wherein said upper clip body has a generally semi-circular shape.

13. The surgical tool assembly according to claim 1, wherein said clip is formed of a resilient material.

14. The surgical tool assembly according to claim 2, further comprising:
   said concavity connecting said first and second grips;
   said first grip having a first radial center and a first diameter;
   said second grip having a second radial center and a second diameter; and
   wherein said second grip is provided between said concavity and said bottom opening, wherein said first and second grips are provided next to each other such that said first radial center of said first grip is radially spaced from said second radial center of said second grip, and wherein said first diameter is larger than said second diameter.

15. The surgical tool assembly according to claim 1, wherein said tool is actuable within a patient's body.

16. The surgical tool assembly according to claim 1, wherein said tool is one of a clip applier, forceps, scissors, grasper, punch, specula, a laparoscopic instrument, or clamp.

17. The surgical tool assembly according to claim 1, wherein said second grip is configured to contract and expand as a result of flexing of said concavity.

18. The surgical tool assembly according to claim 1, wherein said first and second grips are in communication with each other via a passage extending between an inner surface of said first grip and an inner surface of said second grip.

19. The surgical tool assembly according to claim 18, wherein said passage has a width extending in a direction of a first diameter of said first grip and a second diameter of said second grip, and wherein said width of said passage is less than a length of said first and second diameters.

* * * * *